United States Patent [19]

Templeton

[11] Patent Number: 4,508,896

[45] Date of Patent: Apr. 2, 1985

[54] PROCESS FOR THE SIMULTANEOUS PRODUCTION OF 2-(2-AMINOALKOXY)ALKANOL AND MORPHOLINE

[75] Inventor: James H. Templeton, Austin, Tex.

[73] Assignee: Texaco Development Corporation, White Plains, N.Y.

[21] Appl. No.: 60,266

[22] Filed: Jul. 25, 1979

Related U.S. Application Data

[63] Continuation-in-part of Ser. No. 582,480, May 30, 1975, abandoned.

[51] Int. Cl.³ .......................................... C07D 295/02
[52] U.S. Cl. .................................................. 544/106
[58] Field of Search ........................................ 544/106

[56] References Cited

U.S. PATENT DOCUMENTS

| | | | |
|---|---|---|---|
| 2,529,923 | 11/1950 | Dickey et al. | 544/106 |
| 3,151,112 | 9/1964 | Moss | 544/106 |
| 3,347,926 | 10/1967 | Zech | 260/585 |
| 3,709,881 | 1/1973 | Warner | 544/178 |

FOREIGN PATENT DOCUMENTS

| | | |
|---|---|---|
| 46-32188 | 9/1971 | Japan . |
| 46-32189 | 9/1971 | Japan . |
| 175512 | 3/1965 | U.S.S.R. . |

*Primary Examiner*—Robert W. Ramsuer
*Attorney, Agent, or Firm*—Robert L. Kulason; James L. Bailey

[57] ABSTRACT

A process for simultaneously producing a 2-(2-aminoalkoxy)alkanol compound and a morpholine compound is disclosed wherein an oxydialkanol is contacted with ammonia in the presence of a catalytically effective amount of a hydrogenation/dehydrogenation catalyst at a temperature of from about 190° C. to about 230° C. and at a pressure ranging from about 700 psig to about 2200 psig, said oxydialkanol having the formula:

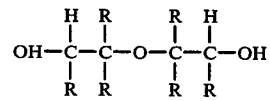

wherein each R is, independently, a hydrogen or a lower alkyl radical; and recovering said 2-(2-aminoalkoxy)alkanol compound and said morpholine compound from the resulting reaction mixture.

2 Claims, No Drawings

PROCESS FOR THE SIMULTANEOUS PRODUCTION OF 2-(2-AMINOALKOXY)ALKANOL AND MORPHOLINE

REFERENCE TO RELATED APPLICATIONS

This application is a continuation-in-part application of copending application Ser. No. 582,480, filed May 30, 1975 abandoned.

BACKGROUND OF THE INVENTION

1. Field of the Invention

This invention relates to a simultaneous preparation of 2-(2-aminoalkoxy)alkanol compound and a morpholine compound and more particularly to the simultaneous production of said compounds at lower pressures optionally in the presence of hydrogen.

2. Prior Art

Morpholine and the C-alkyl substituted morpholine compounds are well known in the art having established utility in a myriad of chemical applications. 2-(2-aminoalkoxy)alkanols are also well known with 2-(2-aminoethoxy)ethanol being the most common such compound. 2-(2-aminoethoxy)ethanol has an established utility, in for example treating natural gas.

Heretofore, it has been known that morpholine could be prepared by contacting a 2-(2-aminoalkoxy)alkanol with ammonia and hydrogen in the presence of a hydrogenation/dehydrogenation catalyst at relatively high operating pressures of about 2,500 psig to about 3,000 psig. This pressure range was previously believed necessary for high yields of morpholine.

While it was known that 2-(2-aminoalkoxy)alkanol along with other complicated amines and by-products were intermediate in this reaction, the prior art teachings indicate the reaction conditions should favor the second or cyclization reaction which involved the use of the above mentioned high operating pressures.

Thus, as disclosed in U.S. Pat. No. 3,151,112, the production of 2-(2-aminoalkoxy)alkanol and morpholine was believed economically unfeasible in that morpholine production would be sacrificed.

Unexpectedly and contrary to the teachings of the prior art we have now found that morpholine and 2-(2-aminoalkoxy)alkanol compounds can be simultaneously produced without an appreciable reduction in yield of the morpholine compound. Contrary to expectations, the production rates of 2-(2-aminoethoxy)ethanol and morpholine are increased when the operating pressures are lower than the previously accepted operating pressures for this process of approximately 2,500–3,000 psig. Such increase in production rate makes possible utilization of a smaller reactor for comparable production. Additionally, because of the lower pressures, lower temperatures may be utilized in attaining a given conversion rate. Further, safer and less expensive operating conditions are possible. The reactors, auxiliary equipment and the like are also less expensive and less catalyst is required.

Another outstanding aspect of the instant invention resides in the fact that by varying the temperature and pressure within a very narrow range one can vary the relative amount of 2-(2-aminoalkoxy)ethanol and morpholine produced.

SUMMARY OF THE INVENTION

According to the broad aspect of the invention, 2-(2-aminoalkoxy)alkanol and morpholine are simultaneously produced by contacting an oxydialkanol compound with ammonia, in the presence of catalytically effective amount of a hydrogenation/dehydrogenation catalyst selected from a group consisting of copper, nickel, chromium, cobalt, manganese, molybdenum, palladium, platinum, rhodium, oxides of said metals and mixtures thereof at a temperature from about 190° C. to about 230° C. substantially in the absence of added hydrogen, and at a pressure ranging from about 700 psig to about 2200 psig; recovering from the resultant reaction mixture the morpholine compound and the 2-(2-aminoalkoxy)alkanol compound.

DESCRIPTION OF THE PREFERRED EMBODIMENT

According to a preferred embodiment, oxydiethanol, also known as diethylene glycol, is contacted with ammonia and hydrogen in the presence of a catalytically effective amount of a hydrogenation/dehydrogenation catalyst consisting of about 60 to 85 mole percent nickel, about 14 to 37 mole percent copper, and about 1 to 6 mole percent chromium in a continuous process. The contacting of the reactants is accomplished at a temperature of from about 200° C. to about 220° C. and at a pressure of about 700 psig to about 2200 psig. The molar ratio of ammonia to oxydiethanol is preferably from about 4:1 to about 8:1 and the space velocities of the liquid feed material, i.e. ammonia and oxydiethanol, are from about 1 g of liquid feed per hour per milliliter of catalyst to about 6 g of liquid feed per hour per milliliter of catalyst. The recovered reaction product which consists primarily of 2-(2-ethoxy)ethanol and morpholine is recovered from the resultant crude reaction product by conventional means such as distillation, extraction and the like.

The oxydialkanol compound that can be utilized in practicing the instant invention can be of the general formula:

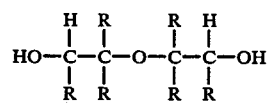

wherein each R is, independently, a hydrogen or a lower alkyl radical such as for example methyl, ethyl or the like. The preferred oxydialkanol compound is oxydiethanol of the above formula wherein each R is, independently, hydrogen.

A large number of catalysts may be employed in practicing the instant invention. These catalytic materials may be generally characterized as hydrogenation catalysts, or as hydrogenation/dehydrogenation catalysts. Examples include copper, nickel, chromium, cobalt, manganese, molybdenum, palladium, platinum, rhodium, oxides of such metals, and mixtures thereof. A particularly preferred catalyst is characterized by having the composition calculated in mole percent on an oxide-free basis of 60–85% nickel, 14–37% copper and 1–6% chromium with the preferred proportions being 72–78% nickel, 20–25% copper and 1–3% chromium. A greatly preferred catalyst is one in which the active components consist essentially of about 75 mole percent nickel, about 23 mole percent copper and about 2 mole percent chromium, as disclosed specifically in U.S. Pat. No. 3,152,998.

phorus as $P_2O_5$, basis total catalyst plus support (alumina support).

TABLE 1

| Run No. | Catalyst | Space Velocity, g/Hr./Ml. Cat. | Mole Ratio $NH_3$/DEG | Reaction Temp., °C. | Reaction Pressure, psig | DEG Conversion, % | % Yield, Basis Converted DEG | | | Wt. Ratio Heavies Morpholine | Production Rates, g/Hr./Liter Cat. | | |
|---|---|---|---|---|---|---|---|---|---|---|---|---|---|
| | | | | | | | Morpholine | DGA | Heavies | | Morpholine | DGA | DGA + Morpholine |
| 1 | A | 1.92 | 5.89 | 210.2 | 1025 | 53.4 | 36.8 | 55.7 | 5.2 | 0.125 | 111.0 | 202.4 | 313.4 |
| 2 | A | 1.95 | 6.12 | 211.0 | 2715 | 37.7 | 43.4 | 48.9 | 3.4 | 0.072 | 87.8 | 119.3 | 207.1 |
| 3 | B | 2.05 | 6.31 | 210.8 | 1000 | 54.8 | 45.8 | 46.4 | 4.9 | 0.097 | 140.5 | 171.8 | 312.3 |
| 4 | B | 1.99 | 5.91 | 211.5 | 2700 | 27.4 | 42.6 | 52.9 | 2.7 | 0.058 | 64.1 | 96.0 | 160.1 |
| 5 | C | 0.93 | 5.91 | 220.6 | 1000 | 33.1 | 30.7 | 61.3 | 4.7 | 0.140 | 22.7 | 54.7 | 77.4 |
| 6 | C | 0.91 | 5.82 | 219.5 | 2660 | 28.9 | 30.4 | 58.7 | 9.1 | 0.273 | 19.6 | 45.6 | 65.2 |

The ratio of reactant, i.e. the ratio of ammonia to oxydiethanol, or other oxydialkanol used in this process is 1:1 to about 10:1 although a molar excess of ammonia produces increased yields of the morpholine product. Optimum yields are obtained when the molar ratio of ammonia to the oxydiethanol is about 6:1. It is not necessary that the ammonia employed be anhydrous, although this is preferred.

The space velocities of the feed, namely, the ammonia and the glycol, may vary from about 1 grams of the liquid feed/hour/milliliter of catalyst, to about 6 grams of liquid feed/hour/milliliter of catalyst. As noted above, the temperature range for the present invention is between about 190° C. and about 230° C. and it is preferably within the range of about 200° C. to about 220° C. depending upon the reactants utilized.

It will be realized by those skilled in the art that an outstanding advantage of the instant process resides in the fact that the relative yields of morpholine and 2-(2-aminoethoxy)ethanol can be varied by a slight variation of reaction conditions while the production rate of the combined products remains high. Thus, one can achieve a substantial yield of 2-(2-aminoethoxy)ethanol which simultaneously maintaining morpholine production rates comparable to or better than those obtained by previously known methods.

For commercial operations, the process of this invention is carried out in a reductive atmosphere, using hydrogen. Although small amounts of hydrogen are present during the reaction from the activated catalyst materials and as a by-product, it is preferred that hydrogen be added in the feed system to maintain catalystic activity. The process of the instant invention can be practiced wherein added hydrogen is substantially absent, but this embodiment is not preferred because of reduced catalyst activity.

The following Table 1 is a summary of the results of six different runs, using the method of this invention in a manner hereinafter described in connection with Examples 1-6, explained hereinafter. In Table 1, "DEG" refers to diethylene glycol, the "Heavies" is a grouping of all products heavier than diethylene glycol, i.e. mole weight greater than 106.12, and the catalysts are as follows: Catalyst A is a nickel, copper, chromium catalyst containing about 72 mole percent nickel, about 22 mole percent copper, and about 6 mole percent chromium, basis active components; catalyst B is a nickel-copper catalyst containing about 77 mole percent nickel, about 23 mole percent copper, basis active components; and catalyst C is a supported catalyst containing about 17 weight percent cobalt and about 3.5 weight percent chromium plus about 0.6 weight percent phosphorus as $P_2O_5$, basis total catalyst plus support (alumina support).

EXAMPLE I

The reactor used for the continuous preparation of 2-(2-aminoethoxy)ethanol and morpholine for run 1, listed in Table 1, consisted of a tubular pressure vessel measuring 1¼ inches inside diameter by 29 inches long. This vessel was constructed of stainless steel. This vertically mounted vessel was electrically heated by means of external strip heaters mounted on the reactor body. A thermowell constructed of ¼ inch o.d. tubing extended upward from the bottom closure a distance of 27 inches in the center of the reactor. Thermo-couples mounted in this thermowell were used for measuring and controlling reaction temperature.

In run 1, the reactor was charged with 510 ml of pelleted nickel-copper-chromium oxide catalyst in which the active components consisted essentially of 72.3 mole % nickel, 21.7 mole % copper, and 6.0 mole % chromium. A 50 wt. % aqueous solution of diethylene glycol (DEG) was pumped at a rate of 666 g/hour through a preheater into the bottom of the reactor. Anhydrous liquid ammonia was pumped separately at a rate of 316 g/hour through a preheater and pre-mixed with the DEG solution just prior to entering the bottom of the reactor. A compressed gas stream composed of about 75 mole % hydrogen and about 25 mole % nitrogen was metered through a rotameter into the bottom of the reactor at a rate of 76 liters/hour expressed at 0° C. and one atmosphere. The combined feeds then flowed upward through the catalyst bed in the reactor. The reactor effluent leaving the top of the reactor was cooled to about 30° C. in a water-cooled heat exchanger. This cooled effluent was passed through a back-pressure regulator adjusted to hold the desired pressure in the reactor. The effluent from this back-pressure regulator was discharged into a receiver at atmospheric pressure in which gaseous products were separated from liquid products.

In run 1, the reactor temperature and pressure were lined out at 210° C. and 1,025 psig, respectively, for a two-hour pre-run period to establish steady-state conditions. Operations then entered a 1½ hour on-stream period during which flow rates, temperatures, and pressure were measured and recorded.

Crude reaction products were analyzed by gas-liquid chromatography. These products were then distilled to obtain a more reliable determination of the morpholine production.

Data and results of this run are presented in Table 1. Conversion of DEG was 53.4% in this run. Yields of DGA and morpholine were 55.7% and 36.8%, respectively, basis converted DEG. Production rates of DGA and morpholine were 202.4 and 111.0 g/hour/liter catalyst, respectively.

EXAMPLE II

Run 2 on Table 1 was carried out identically to Run 1 in Example I except that the reaction pressure was 2,700 psig in run 2. Data and results for this run are presented in Table 1, and it is to be noted that the production rate of DGA and morpholine was lower at 2,700 psig than at 1,000 psig reaction pressure, thus demonstrating the unexpected and unobvious results of increased productivity of the reaction products, DGA and morpholine, at the decreased pressure of about 1,000 pounds per square inch gauge (psig) as compared to the reaction pressure of approximately 2,700 psig which has been the accepted operating pressure in the morpholine process up to this time.

EXAMPLE III

Run 3 was carried out identically to run 1 of Example I except for the catalyst used. In this example 510 ml of pelleted nickel-copper oxide catalyst in which the active components consisted essentially of 76.9 mole % nickel and 23.1 mole % copper was charged to the reactor. The data and results of this run at 1,000 psig are presented in Table 1.

EXAMPLE IV

Run 4 was carried out identically to Run 3 of Example III except that the reaction pressure was 2,700 psig. The data and results for run 4 at 2,700 psig are listed in Table 1, and here again the combined production rates of DGA and morpholine were higher at 1,000 psig than at 2,700 psig.

EXAMPLE V

Run 5 was made in a continuous tubular reactor similar to run 1 described in Example I. This run was made with the reactor filled with 470 ml of a cobalt-chromium catalyst applied to alumina support. This supported catalyst contained 17 wt. % cobalt and 3.5 wt. % chromium; moreover, it contained 0.6 wt. % phosphorus expressed as phosphorus pentoxide ($P_2O_5$) with reference to the total of catalyst and carrier. A 50 wt. % aqueous solution of DEG was pumped at a rate of 292 g/hour through a preheater into the bottom on the reactor. Anhydrous liquid ammonia was pumped separately at a rate of 136 g/hour and preheated prior to entering the bottom of the reactor. This gave a feed ratio of 5.91 moles $NH_3$/mole DEG and a space velocity of 0.93 g liquid feed/hour/ml catalyst. A compressed gas stream composed of 75 mole % hydrogen and 25% mole nitrogen was metered through a rotameter into the bottom of the reactor at a rate of 76 liters/hour expressed at 0° C. and one atmosphere. Reaction temperature was controlled at 220.6° C. and reaction pressure was regulated at 1,000 psig during this run. Reaction products were collected, distilled and analyzed as described in Example I. Results of run 5 are presented in Table 1. Production rates of DGA and morpholine were 54.7 and 22.7 g/hour/liter catalyst, respectively, in this run at 1,000 psig reaction pressure.

EXAMPLE VI

Run 6 was a single run identical to run 5 of Example V except that reaction pressure was 2,660 psig in this run. Production rates of DGA and morpholine were 45.6 and 19.6 g/hour/liter catalyst, respectively. As in the other examples above, the production rates of DGA and morpholine were higher at 1,000 psig than at 2,660 psig at similar temperatures and flow rates.

The following Table 2 presents data with respect to three additional runs numbered 7-9 at different operating conditions, as will be explained hereinafter in connection with Examples VII-IX. The same symbols and abbreviations are used in Table 2 as in Table 1, and the catalyst was the same in all of the runs 7-9 and was a nickel-copper-chromium catalyst containing about 75 mole % nickel, 23 mole % copper, and 2 mole % chromium, basis active components. Specifically, the catalyst contained 75.7 mole % nickel, 22.7 mole % copper, and 1.6 mole % chromium.

TABLE 2

| Run No. | Space Velocity, g/Hr./Ml. Cat. | Mole Ratio $NH_3$/DEG | Reaction Temp., °C. | Reaction Pressure, psig | DEG Conversion, % | % Yield, Basis Converted DEG | | | Wt. Ratio Heavies | Production Rates, g/Hr./Liter Cat. | | |
|---|---|---|---|---|---|---|---|---|---|---|---|---|
| | | | | | | Morpholine | DGA | Heavies | Morpholine | Morpholine | DGA | DGA + Morpholine |
| 7 | 2.06 | 6.40 | 209.5 | 700 | 86.8 | 59.7 | 17.9 | 19.7 | 0.300 | 264.9 | 95.6 | 360.5 |
| 8 | 2.00 | 6.34 | 210.0 | 1400 | 77.2 | 63.5 | 23.4 | 10.2 | 0.145 | 245.3 | 109.0 | 354.3 |
| 9 | 2.03 | 5.97 | 210.5 | 2625 | 53.7 | 58.6 | 30.0 | 7.6 | 0.117 | 159.2 | 98.3 | 257.5 |

EXAMPLE VII

Run 7 was identical to run 1 of Example I except for a difference in catalyst composition and reactor pressure. In this run the reactor was charged with 510 ml of pelleted nickel-copper-chromium oxide catalyst in which the active components consisted essentially of 75.7 mole % nickel, 22.7 mole % copper, and 1.6 mole % chromium. Run 7 was made at a temperature of 209.5° C. and a pressure of 700 psig. The space velocity was 2.06 g liquid feed/hour/ml catalyst and the feed ratio was 6.40 mole $NH_3$/mole DEG.

Results of this run are presented in Table 2. At a reaction temperature of 209.5° C., production rates of DGA and morpholine were 95.6 and 264.9 g/hour/liter catalyst, respectively, giving a total DGA and morpholine production rate of 360.5 g/hour/liter catalyst.

EXAMPLE VIII

An additional run, run 8, was made at an intermediate pressure of 1,400 psig and results are included in Table 2. DGA and morpholine production rates in run 8 were 109.0 and 245.3 g/hour/liter catalyst, giving a combined production rate of 354.3 g/hour/liter catalyst. This was only slightly lower than the 360.5 g/hour/liter obtained at 700 psig but considerably more than the 257.5 g/hour/liter observed at 2,625 psig as reported in Table 2.

EXAMPLE IX

Run 9 was identical to run 7 of Example VII except for a reaction pressure of 2,625 psig. The results are presented in Table 2. At a temperature of 210.5° C., production rates of DGA and morpholine were 98.3 and 159.2 g/hour/liter, respectively, giving a total DGA and morpholine production rate of 257.5 g/hour/liter catalyst, which was considerably lower than the combined production rate reported for Examples VII and VIII at 700 psig operating pressure.

EXAMPLES X-XIII

Here further confirming runs were made showing the advantages of the process of the invention by running said process within the discovered pressure limits.

The reactor of Example I was employed here in the same manner described with the exception that pure hydrogen gas feed was used in these runs instead of the 75 mole % hydrogen-25 mole % nitrogen mixture used there.

Data and results of these four runs are included in Table 3 below. These runs were made at a space velocity of 2 g liquid feed/hour/ml catalyst and a feed mole ratio of 6 moles of ammonia per mole of DEG. Temperature was held constant at 210° C. while reaction pressure was varied from 1,000 to 2,500 psig. As can be noted below, production rates in terms of the key figure of total production of DGA and morpholine begin to decline at about 2200 psig, and at a pressure substantially above 2500 psig, as was seen in earlier runs, the combined production rate materially declines.

Water and DEG were premixed and then fed to a 2-gallon reactor system with ammonia using a feed pump. Feed rates were monitored using 77-gallon feed tanks on scales. Hydrogen in the form of disassociated ammonia (75% hydrogen-25% nitrogen mixture) was also fed to the reactor either before or after the preheater. The preheater was a double pipe exchanger with four loops of ½ inch pipe covered by a 1½ inch jacket. The exchanger surface area was 3.3 square feet. The reactor operated adiabatically with the jacket drain. The reactor effluent passed through a cooler and then a back pressure regulator. The reactor effluent was ammonia-stripped in 77-gallon tanks and then product recovered and analyzed by gas-liquid chromatography. Again products were distilled to obtain a more reliable determination of morpholine production.

In the work summarized below in Table 4 the mole ratio of ammonia to DEG was maintained at about 6:1 through the runs. The space velocity in 2 series of runs (runs 14–17 and runs 18–22) was maintained at about 3 while in runs 22 and 23 the space velocity was maintained at about 2. In runs 24 and 25 the space velocity was maintained at about 4.

As is readily apparent from the data appearing in Table 4, production rates in terms of total production of DGA and morpholine begin to rapidly decline much above about 2200 psig. At around 2500 psig there is a noticable decrease in the production rates.

TABLE 4

| Run No. | Space Velocity g/Hr./Ml. Cat. | Mole Ratio NH$_3$/DEG | Reaction Temp., °C. | Reaction Pressure, psig | DEG Conversion, % | % Yield, Basis Converted DEG | | | Wt. Ratio Heavies | Production Rates, g/Hr./Liter Cat. | | |
|---|---|---|---|---|---|---|---|---|---|---|---|---|
| | | | | | | Morpholine | DGA | Heavies | Morpholine | Morpholine | DGA | DGA + Morpholine |
| 14 | 3.13 | 6.40 | 210.5 | 2500 | 35.2 | 34.14 | 54.93 | 8.98 | 0.258 | 102.02 | 198.11 | 300.13 |
| 15 | 2.98 | 5.30 | 212 | 1600 | 53.6 | 38.83 | 48.53 | 10.73 | 0.264 | 178.62 | 269.42 | 448.04 |
| 16 | 3.12 | 5.75 | 211 | 1300 | 58.2 | 39.38 | 47.67 | 10.83 | 0.265 | 200.86 | 293.43 | 494.29 |
| 17 | 3.08 | 6.23 | 211 | 1000 | 65.1 | 40.27 | 44.67 | 12.87 | 0.308 | 220.98 | 295.83 | 516.81 |
| 18 | 3.13 | 6.23 | 210 | 2500 | 39.0 | 39.3 | 45.9 | 12.19 | 0.300 | 131.29 | 185.06 | 316.35 |
| 19 | 3.36 | 5.90 | 210 | 2200 | 46.0 | 42.9 | 47.7 | 6.88 | 0.155 | 188.34 | 252.73 | 441.07 |
| 20 | 3.26 | 6.40 | 210.5 | 1900 | 51.7 | 43.9 | 45.4 | 7.79 | 0.167 | 200.66 | 250.44 | 451.10 |
| 21 | 3.20 | 6.07 | 209.5 | 1600 | 51.3 | 34.6 | 55.4 | 7.78 | 0.221 | 156.78 | 302.96 | 459.74 |
| 22 | 2.20 | 6.23 | 211 | 2500 | 51.1 | 52.2 | 35.3 | 9.70 | 0.176 | 160.60 | 131.07 | 291.67 |
| 23 | 2.01 | 5.75 | 210 | 1600 | 65.3 | 51.8 | 36.4 | 10.20 | 0.196 | 190.97 | 161.96 | 325.93 |
| 24 | 3.94 | 5.57 | 210 | 2500 | 37.2 | 43.8 | 42.0 | 11.31 | 0.251 | 182.12 | 210.76 | 392.88 |
| 25 | 4.18 | 6.10 | 210 | 1600 | 41.7 | 32.0 | 5711 | 8.66 | 0.257 | 153.72 | 331.03 | 484.75 |

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for simultaneously producing a morpholine compound and a 2-(2-aminoethoxy)ethanol compound, comprising the steps of:

reacting an oxydialkanol with ammonia, in the presence of added hydrogen, over an hydrogenation-dehydrogenation catalyst selected from the group consisting of copper, nickel, chromium, cobalt, manganese, molybdenum, palladium, platinum, rhodium, oxides of said metals, and mixtures thereof;

said reaction taking place within a pressure range of from about 700 psig to about 2200 psig, and within a temperature range of from about 190° C. to about 230° C.;

said oxydialkanol having the formula:

TABLE 3

| Run No. | Space Velocity, g/Hr./Ml. Cat. | Mole Ratio NH$_3$/DEG | Reaction Temp., °C. | Reaction Pressure, psig | DEG Conversion, % | % Yield, Basis Converted DEG | | | Wt. Ratio Heavies | Production Rates, g/Hr./Liter Cat. | | |
|---|---|---|---|---|---|---|---|---|---|---|---|---|
| | | | | | | Morpholine | DGA | Heavies | Morpholine | Morpholine | DGA | DGA + Morpholine |
| 10 | 2.06 | 6.45 | 210.0 | 1000 | 77.11 | 69.65 | 10.56 | 8.74 | 0.122 | 297.33 | 54.41 | 351.74 |
| 11 | 2.01 | 6.23 | 210.3 | 1600 | 71.81 | 68.81 | 8.68 | 7.66 | 0.108 | 272.33 | 41.48 | 313.81 |
| 12 | 1.95 | 5.78 | 210.0 | 2000 | 71.03 | 71.02 | 7.64 | 8.23 | 0.113 | 275.52 | 35.76 | 311.28 |
| 13 | 1.98 | 5.79 | 210.0 | 2500 | 64.22 | 74.29 | 7.11 | 7.11 | 0.102 | 265.31 | 30.65 | 295.96 |

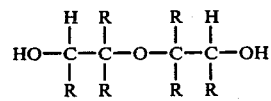

in which R is selected from the group consisting of hydrogen and lower alkyl radicals; and isolating said morpholine compound and said 2-(2-aminoethoxy)ethanol compound from the reaction products.

2. The process of claim 1 wherein: said hydrogenation-dehydrogenation catalyst consists essentially of about 60–85 mole % nickel, about 14–37 mole % copper and about 1–6 mole % chromium.

* * * * *